United States Patent [19]

Depel

[11] 4,304,228
[45] Dec. 8, 1981

[54] OUTSIDE LOCKING TRACHEAL TUBE

[75] Inventor: William Depel, Lowell, Ind.

[73] Assignee: Bivona Surgical Instruments, Inc., Hammond, Ind.

[21] Appl. No.: 167,839

[22] Filed: Jul. 14, 1980

[51] Int. Cl.³ .......................................... A61M 25/00
[52] U.S. Cl. ......................... 128/200.26; 128/207.17; 128/912
[58] Field of Search ............... 128/200.26, 207.14, 128/207.15, 207.17, 6, 7, 349 R, 912; 285/158, 176

[56] References Cited

U.S. PATENT DOCUMENTS

| | | | |
|---|---|---|---|
| 2,820,457 | 1/1958 | Phillips | 128/200.26 |
| 2,888,017 | 5/1959 | Wallace | 128/7 |
| 3,039,469 | 6/1962 | Fountain | 128/200.26 |
| 3,169,529 | 2/1965 | Koenig | 128/207.14 |
| 3,640,282 | 2/1972 | Kamen et al. | 128/207.15 |
| 4,258,721 | 3/1981 | Parent et al. | 128/6 |

Primary Examiner—Henry J. Recla
Attorney, Agent, or Firm—Emrich, Root, Lee, Brown & Hill

[57] ABSTRACT

A tracheotomy tube of the type embodying inner and outer cannulas, with the inner cannula being removable from and insertable into the outer cannula and having a flange projecting outwardly therefrom in position to be disposed in a recess in the outer cannula for holding the cannulas against rotation relative to each other, and with the outer cannula embodying a collar rotatable into and out of overlying relation to the recess for selectively securing the flange in the recess and permitting withdrawal therefrom, respectively.

13 Claims, 7 Drawing Figures

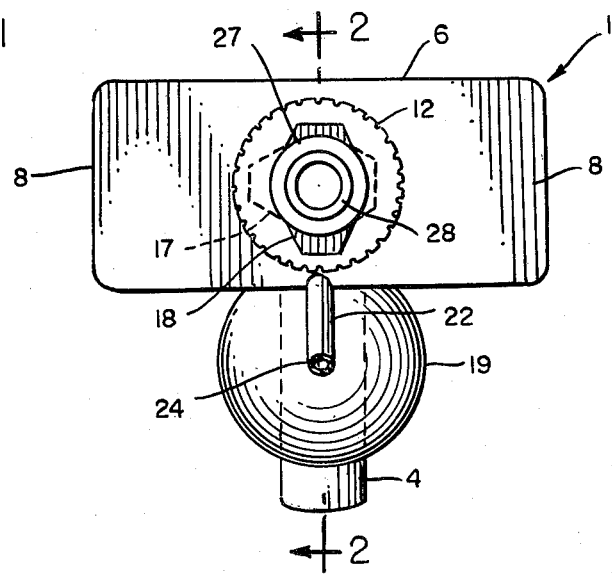
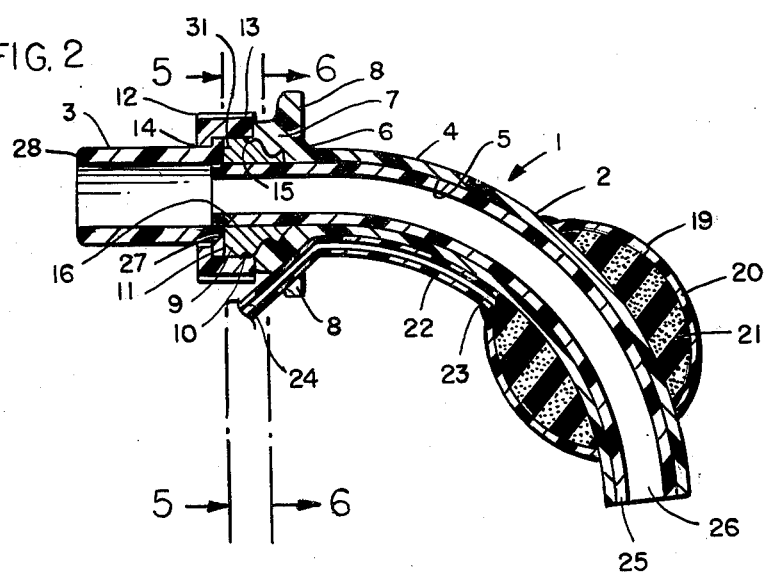
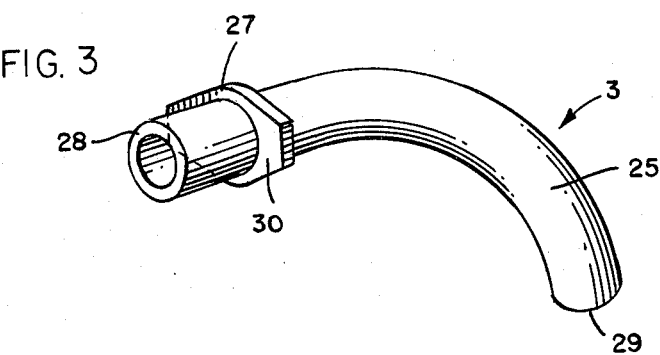

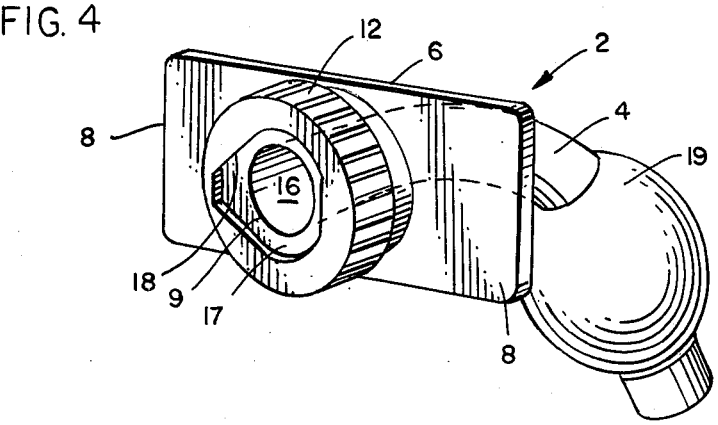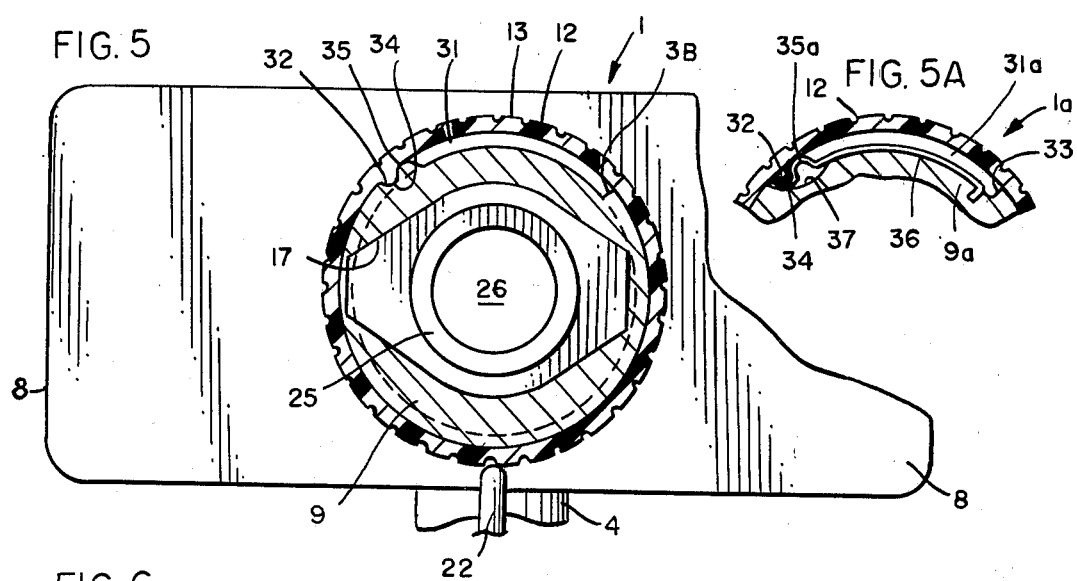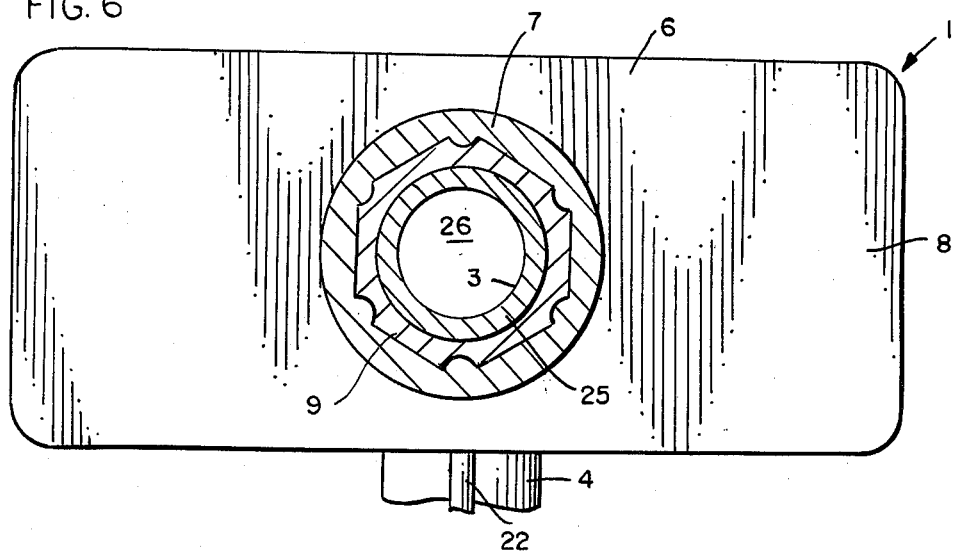

OUTSIDE LOCKING TRACHEAL TUBE

BACKGROUND OF THE INVENTION

The present invention relates to tracheotomy tubes, and, more particularly, to tracheotomy tubes of the type that embody an inner cannula that may be removed for cleaning, and the like, without removing the entire tube.

A primary object of the present invention is to afford a novel tracheotomy tube.

Another object of the present invention is to afford a novel tracheotomy tube of the type embodying inner and outer cannulas.

A further object of the present invention is to afford a novel tracheotomy tube of the aforementioned type which is well adapted for insertion through an incision through a person's neck into the trachea of the person.

As is well known in the art, one of the problems with the use of tracheotomy tubes inserted through a person's neck into the trachea is that the tube, from time to time, becomes coated or clogged with phlegm, necessitating the cleaning of the tube in order for it to properly operate. In early forms of tracheotomy tubes, this often necessitated the removal of the complete tube from the person's neck for cleaning and subsequent insertion back into the person's trachea. This, of course, was a somewhat difficult procedure that was often irritating, if not downright painful to the patient. Also, such removal and reinsertion of the complete tube entailed the risk of injury to the patient.

In relatively recent years tracheotomy tubes, which embody an inner cannula removably mounted in an outer cannula, have been developed. With such construction, when the tube becomes undesirably coated or obstructed by phlegm, or the like, the inner cannula may be removed from the outer cannula, cleaned and again inserted into the outer cannula, while leaving the outer cannula in place in the patient's neck. Such construction, of course, has the advantage of reducing the risk of injury to the patient as well as reducing the irritation or pain that the patient suffers in such an operation. Also, with the inner cannula being of substantially the same length as the outer cannula, and being of such a cross-sectional size that it fits in the outer cannula with a relatively snug, but freely slidable fit, the danger of injury to the patient, during removal and reinsertion of the inner cannula, is reduced, and the outer cannula is rendered substantially "self-cleaning," the movement of the inner cannula into and out of the outer cannula tending to keep the outer cannula clear and unclogged. Such tracheal tubes have been heretofore known in the art, being shown, for example, in U.S. Pat. Nos. 3,659,612; 3,688,774; 3,693,624 and 4,009,720. It is an important object of the present invention to afford improvements over such tracheotomy tubes heretofore known in the art.

Tracheotomy tubes heretofore known in the art, which embodied an inner cannula removably mounted in an outer cannula, have commonly had several inherent disadvantages, such as, for example, being complicated in construction and operation; being difficult to connect or disconnect; or the inter-connection between the inner and outer cannulas being such that the cannulas could relatively readily be accidentally disconnected from each other, such as, for example, by a patient thrashing around in his sleep, and the like. It is another important object of the present invention to overcome such disadvantages.

A further object of the present invention is to afford a novel tracheotomy tube embodying an outer cannula for insertion into a patient, and an inner cannula for insertion into the outer cannula for affording the passageway through which the patient may breathe.

Another object is to afford a novel tracheotomy tube of the aforementioned type wherein the inner and outer cannulas are releasably connected together in a novel and expeditious manner.

An object ancillary to the foregoing is to enable such inner and outer cannulas to be quickly and easily connected and disconnected.

Another object of the present invention is to afford a novel tracheotomy tube of the aforementioned type, wherein the construction of which is such as to insure that twisting or turning on the inner cannula, such as, for example, by reason of the patient in whom it is inserted thrashing around in his sleep, will not be effective to disconnect the two cannulas from each other.

A further object of the present invention is to afford a novel tracheotomy tube of the aforementioned type which embodies a novel inter-connection between the inner and outer cannulas thereof.

Another object of the present invention is to afford a novel tracheotomy tube of the aforementioned type embodying a novel inter-connection between the inner and outer cannulas, wherein, when the inner cannula is disposed in operative position in the outer cannula, it is held against rotation relative to the latter, and the inter-connection between the two cannulas embodies a portion of the outer cannula, which in making the inter-connection between the cannulas is moved into a position wherein the inner cannula is prevented from being accidentally withdrawn therefrom either by pulling on the inner cannula or by twisting or turning forces being applied to the inner cannula.

A further object of the present invention is to afford a novel tracheotomy tube of the aforementioned type which embodies a relatively soft, flexible outer cannula for protecting a patient wearing the same against injury, as well as protecting such a patient during insertion and removal of the tube.

Another object of the present invention is to afford a novel tracheotomy tube of the aforementioned type, which is practical and efficient in operation and which may be readily and economically produced commercially.

Other and further objects of the present invention will be apparent from the following description and claims and are illustrated in the accompanying drawings which, by way of illustration, show preferred embodiments of the present invention and the principles thereof and what I now consider to be the best modes in which I have contemplated applying these principles. Other embodiments of the invention embodying the same or equivalent principles may be used and structural changes may be made as desired by those skilled in the art without departing from the present invention and the purview of the appended claims.

DESCRIPTION OF THE DRAWINGS

In the drawings:

FIG. 1 is a front elevational view of a tracheotomy tube embodying the principles of the present invention;

FIG. 2 is a longitudinal sectional view taken substantially along the line 2—2 in FIG. 1;

FIG. 3 is a front perspective view of the inner cannula embodied in the tracheotomy tube shown in FIG. 1;

FIG. 4 is a front perspective view of the outer cannula embodied in the tracheotomy tube shown in FIG. 1;

FIG. 5 is a fragmentary detail sectional view taken substantially along the line 5—5 in FIG. 2;

FIG. 5A is a fragmentary sectional view similar to a portion of FIG. 5, but showing a modified form of the present invention; and FIG. 6 is a fragmentary, detail sectional view taken substantially along the line 6—6 in FIG. 2.

DESCRIPTION OF THE EMBODIMENTS SHOWN HEREIN

A tracheotomy tube 1, embodying the principles of the present invention, is shown in FIGS. 1-5 and 6 of the drawings to illustrate the presently preferred embodiment of the present invention.

The tracheotomy tube 1 embodies an outer cannula 2, FIG. 4, and an inner cannula 3, FIG. 3, the inner cannula 3 being removably mounted in the outer cannula 2, as illustrated in FIGS. 1, 2, 5 and 6, when the tracheotomy tube 1 is disposed in operative position in a person, as will be discussed in greater detail presently.

The outer cannula 2 embodies a main body member 4 in the form of an elongated tube having a bore 5 extending longitudinally therethrough, the body member 4 terminating at its proximal end in an enlarged portion in the form of a radially outwardly projecting flange 6 embodying a central body portion 7 having two flaps or ears 8 projecting outwardly in diametrically opposite directions therefrom. An annular collar or bushing 9 is mounted in the central body portion 7 of the flange 6 in axial alignment therewith, FIG. 2, the bushing 9 preferably being non-rotatably secured to the flange 6 by suitable means such as, for example, an adhesive, not shown.

The bushing 9 has an annular groove 10 extending therearound in rearwardly spaced relation to the front face 11 thereof, and in the assembled outer cannula 2, an annular collar 12, embodying an outer sidewall 13, and having a front wall 14 and a rear wall 15 projecting radially inwardly from the front and rear edges of the sidewall 13, is rotatably mounted on the bushing 9 with the rear wall 15 retainingly disposed in the annular recess 10. Preferably, when the collar 12 is disposed in operative position on the bushing 9, the rear wall 15 is disposed in abutting engagement with the front face of the flange 6.

The bushing 9 has a bore 16 extending therethrough, which, in the assembled outer cannula 2 is disposed in axial alignment with the bore 5 in the main body member 4. An elongated recess 17 is formed in the outer face 11 of the bushing 9, FIGS. 1, 4 and 5, the recess 17 being elongated in a direction transverse to the longitudinal axis of the bore 5 and 16 through the outer cannula 2. Preferably, the recess 17 is oblong or substantially eliptical in shape, and extends longitudinally in diametrically opposite directions from the bore 16, as shown in FIG. 5. However, as will be appreciated by those skilled in the art, this particular shape is merely by way of illustrating the presently preferred embodiment of the present invention, and other shapes of recesses, such as, for example, elongated recesses extending outwardly on one side of the bore 16, only, may be used without departing from the purview of the broader aspects of the present invention.

The collar 12 has an opening 18, which is complimentary in size and shape to the recess 17, transversely to the longitudinal axis of the bore 16 through the bushing 9, FIG. 4. The collar 12 is rotatable around the bushing 9, such rotation being effective to move the opening 18 from the position shown in FIG. 4, wherein it is disposed in aligned relation to the recess 17, to other positions, wherein the recess 18 is disposed out of alignment with the recess 17, such as shown in FIG. 1, for a purpose which will be discussed in greater detail presently.

Preferably, the tracheotomy tube 1 embodies a cuff for sealingly engaging the inside of the trachea of a person into which a tracheotomy tube has been inserted. The cuff may be of any suitable form, such as, for example, any one of several of the inflatable balloon cuffs heretofore available on the market. However, preferably, the cuff 19 on the outer cannula 2 of the tracheotomy tube 1 comprises a normally expanded balloon cuff of the type disclosed in U.S. Pat. No. 3,640,282, issued to Jack M. Kamen on Feb. 8, 1972, such a cuff embodying an air impervious cover 20, which is normally, resiliently maintained in an expanded position away from the body member 4 of the outer cannula 2 by a resilient member 21 mounted therein, the resilient member 21 being made of suitable material, such as, for example, sponge rubber. The cuff 19 has a tube 22, having one end 23 connected to the interior of the cover 20 and the other end 24 projecting outwardly away from the cuff 19.

As discussed in greater detail in the aforementioned Kamen U.S. Pat. No. 4,640,282, with this construction, the cuff 19 is normally maintained in inflated condition by the resilient member 21, and, when it is desired to insert the outer cannula 2 into the trachea of a patient air is withdrawn from the interior of the cover 20 by applying suction to the end portion 24 of the tube 22 and thereby collapsing the cuff 19. After the cannula 2 has been inserted into proper position in the trachea of the patient, the suction on the tube 22 may be released to thereby permit atmospheric air to flow back into the cuff 19 and thereby permit it to expand into sealing engagement with the inner surface of the trachea of the patient, the resilient material 21 affording a soft, yielding pressure for effecting such sealing engagement.

Preferably, the body portion 4 of the outer cannula 2, and the cover member 20 of the cuff 19 mounted thereon is made of relatively soft, flexible, resilient plastic material, such as, for example, polyethylene, and the bushing 9 is made of relatively hard, corrosion resistant material, such as, for example, aluminum stainless steel, or a suitable plastic material, such as the acrylic resin, known as Plexiglas. With such construction, effective protection against corrosion is afforded. Also, with the body portion 4 being made of relatively soft, flexible material, the possibility of damage to the patient's delicate membranes, during insertion and withdrawal of the outer cannula 2, and even when the outer cannula 2 is disposed in operative position in the patient, is minimized.

Preferably, the body member of the outer cannula 2 is gently curved in its normal, unrestrained position, to facilitate the insertion of the distal end thereof into the trachea of a patient, through an incision made in the neck of the patient. However, with the body portion 4 of the outer cannula 2 being made of the aforementioned soft, flexible material, the importance of having this curvature of the body portion 4 is not as great as if the body portion 4 were made of stiffer, more unyielding material, such as those from which outer cannulas of tracheotomy tubes heretofore known in the art have been commonly made, namely, metal or substantially hard rigid plastics, and the like, the body portion 4 of the outer cannula 2 tending to conform itself to the position of the surrounding tissues during insertion and removal of the cannula 2 into and out of such a patient.

The inner cannula 3 also embodies a main body member 25 in the form of an elongated tube having a bore 26 extending longitudinally therethrough, FIGS. 2 and 3. The body member 25 terminates at its proximal end in an enlarged portion in the form of a radially outwardly projecting flange 27, with a connector portion 28 projecting forwardly beyond the flange 27, FIGS. 2 and 3. The connector portion 28 is afforded for the purpose of connecting the inner cannula 3 to a source of oxygen, or the like, not shown, suitable tubes, not shown, being mounted on the connector portion 28, in a manner well known in the art, for this purpose. Preferably, the connector portion 28 is of larger outside diameter than the body portion 25 of the inner cannula 3, so as to thereby afford a substantial connector surface for connection to oxygen tubes, and the like, but is of smaller outside diameter than the lateral width of the flange 27, so that, the flange 27 affords an abutment member for limiting the distance that such a connecting tube may be moved along the inner cannula 3.

The flange 27 is of complimentary size and shape, transversely to the bore 26 through the body member 25, as the recess 17, transversely to the bore 5 through the outer cannula 2. The outer diameter of the body member 25 of the inner cannula 3 is such that the body member 25 may be inserted into the outer cannula 2 through the opening 18 in the collar 12, and is received in the bore 5 of the outer cannula 2 with a relatively snug, but freely slidable fit.

The flange 27 is of the same thickness, axially of the inner cannula 3 as the depth of the recess 17 in the bushing 9. With this construction, it will be seen that, with the collar 12 disposed in the position shown in FIG. 4, wherein the opening 18 therethrough is disposed in axial alignment with the recess 17 in the bushing 9, the inner cannula 3 may be inserted into the outer cannula 2 by inserting the distal end 29 thereof inwardly through the opening 18 in the collar 12, and moving the inner cannula 3 progressively along the bore 16 and 5 of the outer cannula 2. When the inner cannula 3 is disposed in fully inserted position in the outer cannula 2, the flange 27 on the inner cannula 3 is disposed in seated relation to the recess 17 in the bore 9. When this occurs, the outer face 30 of the flange 27 is disposed rearwardly of the front wall 14 of the collar 12, so that the collar 12 may be rotated around the bushing 9 into position, such as shown in FIG. 1, wherein the opening 18 therethrough no longer is disposed in axial alignment with the recess 17. In this position of the collar 12, the front wall 14 thereof is disposed in overlapping relation to the flange 27, and is effective to afford a positive restraint against axial movement of the inner cannula 3 outwardly from the outer cannula 2. Also, it will be seen that, with the flange 27 being held against rotation around the longitudinal axis of the outer cannula 2, by reason of its complimentary, lateral engagement in the recess 17, the tracheotomy tube 1, when thus assembled, is effectively held against accidental disconnection of the cannulas 2 and 3 by either axial or torsional forces being applied to the inner cannula 3. This, it will be seen, affords effective protection against the cannulas 2 and 3 being accidentally disconnected from each other by reason of a patient, connected thereto, thrashing around in his sleep, and the like.

Also, it will be seen that although the collar 12 is so constituted and arranged that it may be readily rotated either by an attendant or by the patient, himself, for intentionally connecting or disconnecting the cannulas 2 and 3, it is disposed in such position on an assembled tracheotomy tube 1 that it is not dangerously exposed to any accidental rotational movements being applied thereto.

To further guard against accidental rotation of the collar 2 on the assembled tracheotomy tube 1, the bushing 9 has an arcuate-shaped annular recess 31 formed in the front edge of its annular surface, FIGS. 2 and 5. The ends of the annular recess 31 are defined by end walls 32 and 33 thereof which afford abutments for a purpose which will be discussed in greater detail presently. The collar 12 has another abutment, in the form of a ridge or pimple 34 projecting radially inwardly from the sidewall 13 thereof. The abutment 34 is of such size, and is so disposed on the collar 12 that, during rotation of the collar 12 from locked position, as shown in FIGS. 1 and 5, wherein the abutment 34 is disposed in engagement with the abutment 32, to the unlocked position, shown in FIG. 4, the abutment 34 moves along the recess 31 into engagement with the abutment 33. Thus, it will be seen that in the preferred form of the abutment member 1, shown in the drawings, rotation of the collar 12 around the bushing 9 is limited to the distance of movement of the abutment member 34 between the abutment members 32 and 33. Preferably, this is in the nature of a substantal acute angle, such as, for example, ninety degrees. Thus, when the collar 2 has been moved from fully unlocked position to fully locked position, the opening 18 is located a substantial distance from the alignment with the recess 17 necessary for removal of the inner cannula 3 from the outer cannula 2.

In the preferred form of the present invention, the bushing 9 also has an abutment 35 disposed in the recess 31 in relatively closely spaced relation to the abutment 32. The abutment 35 projects radially outwardly in the recess 31 and, preferably, is rounded, so that it merely affords a releasable, retarding engagement with the abutment 34 during passage of the latter along the recess 31, the latter being able to ride upwardly over the abutment 35, camming the sidewall 13 of the collar 12 outwardly as it does so.

The spacing of the abutment 35 relative to the abutment 32 preferably is such that when the collar is disposed in fully locked position, the abutment 34 is abuttingly engaged by both the abutments 32 and 35. With this construction, disposition of the collar 12 in the desired locked position is effectively indicated, with the resistance of the abutment 35 to rotation of the collar 12 to unlocked position affording additional security against accidental rotation thereof in such direction.

In FIG. 5A, a modified form of the present invention is shown, and parts which are the same as parts shown in FIGS. 1-5 and 6 are indicated by the same reference numerals, and parts which are similar to but differ from parts shown in FIGS. 1-5 and 6 are indicated by the same reference numerals with the suffix "a" added.

The tracheotomy tube 1a shown in FIG. 5a is the same in construction and operation as the tracheotomy tube 1 shown in the other drawings except that the arcuate recess 31a has been modified to accommodate a hair spring 36, which is mounted therein and secured to the bushing 9a, the hair spring 36 embodying a U-shaped portion 35a, which takes the place of the abutment member 35 in the tracheotomy tube 1. The U-shaped portion 35a affords a resilient, abutment member, which is disposed in the same position in the recess 31a as the abutment member 35 is disposed in the recess 31.

With this construction, when the abutment member 34 on the collar 12 of the tracheotomy tube 1a is disposed in the "locked" position thereof, as shown in FIG. 5a, it is disposed between, and in abutting engagement with the abutment member 32 and the abutment member 35a. Rotation of the collar 12 from this position in a clockwise direction, as viewed in FIG. 5a, is effective to move the abutment member 34 over the abutment member 35a, the latter being depressed by such movement into a recess 37 formed in the arcuate recess 31a. Such construction affords effective holding of the collar 11 in the aforementioned "locked" position, while still enabling the collar 12 to be intentionally, manually rotated from that position into position wherein the abutment member 34 is disposed in abutting relation to the abutment member 33, when it is desired to rotate the opening 18 into aligned position with the recess 17.

From the foregoing it will be seen that the present invention affords a novel tracheotomy tube of the type embodying an outer cannula, with an inner cannula which may be inserted into and removed from the latter, the tracheotomy tube of the present invention affording an effective connector for reliably holding the inner and outer cannulas in assembled relation to each other.

Also, it will be seen that the present invention affords a novel tracheotomy tube, the construction and operation of which is effective to insure against the accidental disconnecting of the inner cannula from the outer cannula by pulling, or twisting, or turning forces being applied to the inner cannula, such as, for example, those that occur if a patient is thrashing around in his sleep.

In addition, it will be seen that the present invention affords a novel tracheotomy tube which is practical and efficient in operation and which may be readily and economically produced commercially.

Thus, while I have illustrated and described the preferred embodiments of my invention, it is to be understood that these are capable of variation and modification and I therefore do not wish to be limited to the precise details set forth, but desire to avail myself of such changes and alterations as fall within the purview of the following claims.

I claim:
1. A tracheotomy tube comprising
   a. an outer, elongated cannula, and
   b. an inner, elongated cannula,
   c. each of said cannulas having
      (1) a proximal end portion,
      (2) a distal end portion, and
      (3) a bore extending longitudinally therethrough,
   d. said inner cannula being removably mounted in said bore of said outer cannula with a snug, freely slidable fit,
   e. said outer cannula comprising
      (1) a tubular body portion
         (a) forming said distal end of said outer cannula, and
         (b) extending to said proximal end of said outer cannula terminating in a free end face,
      (2) an enlarged portion on said proximal end thereof defining an end face, and
      (3) a collar rotatably mounted on said enlarged portion for rotation on said enlarged portion around the longitudinal axis of said bore in said outer cannula,
   f. said collar having a front wall slidably disposed over said end face of said enlarged portion and defining the free end face of said proximal end of said outer cannula,
   g. said enlarged portion having an elongated recess in said end face thereof with segments of the perimeter being substantially non-parallel to the perimeter of said bore in said outer cannula,
   h. said recess projecting radially outwardly from said bore in said outer cannula,
   i. said front wall having an opening therethrough,
   j. said opening being complimentary in size and shape to said recess in said end face of said enlarged portion of said outer cannula and being aligned therewith,
   k. said collar being rotatable on said enlarged portion between
      (1) one position wherein said opening is disposed in parallel alignment with said recess, and
      (2) another position wherein said opening is disposed out of said parallel alignment with said recess,
   l. said inner cannula proximal end having an elongated flange projecting radially outwardly therefrom and being sized and shaped to fit in said recess,
   m. said inner cannula being movable axially through said opening into and out of position in said outer cannula wherein said flange is disposed in said recess when said collar is disposed in said one position, and
   n. said collar being rotatable from said one position to said other position, when said flange is so disposed in said recess, to thereby dispose said front wall in overlying relation to said flange in position to prevent movement of said inner cannula out of said outer cannula.

2. A tracheotomy tube as defined in claim 1, and in which
   a. said flange is substantially complimentary
      (1) in size and shape to said recess, transversely of said bore in said outer cannula, and
      (2) in thickness to the depth of said recess, longitudinally of the longitudinal axis of said bore in said outer cannula.

3. A tracheotomy tube as defined in claim 1, and in which
   a. said tubular body portion is composed of soft, resilient, flexible material,
   b. said enlarged portion comprises
      (1) a flange integral to said tubular body portion, and
      (2) a bushing mounted in said last mentioned flange.

4. A tracheotomy tube as defined in claim 3, and in which
   a. said bushing has an arcuate-shaped, radially outwardly facing annular recess extending around an outer peripheral portion thereof between two abutment members defining the opposite longitudinal opposite extremities of said annular recess, and b. said collar has an inner portion disposed in position to abuttingly engage respective ones of said abutment members when said collar is disposed in corresponding ones of said one and other positions, to thereby limit said rotation of said collar to rotation between said one and other positions.

5. A tracheotomy tube as defined in claim 4, and in which a. said bushing has another abutment member disposed in said annular recess in position to yieldingly abuttingly engage said inner portion of said collar to yieldingly hold said collar in said another position against movement toward said one position when said collar is disposed in said another position.

6. A tracheotomy tube as defined in claim 5, and in which a. said other abutment member comprises a member disposed in said annular recess in radially outwardly projecting relation thereto and in position therein for said inner portion of said collar to yieldingly pass thereacross during rotation of said collar between said one and other positions.

7. A tracheotomy tube as defined in claim 6, and in which a. said other abutment member comprises an integral portion of said bushing.

8. A tracheotomy tube as defined in claim 6, and in which a. said other abutment member comprises a substantially U-shaped hair spring mounted in said annular recess in radially outwardly projecting relation thereto.

9. A tracheotomy tube as defined in claim 6, and in which a. said one and other positions of said collar are displaced from each other the substantial part of ninety degrees.

10. A tracheotomy tube as defined in claim 3, and in which a. said last mentioned flange includes diametrically opposite outwardly projecting portions for attachment to a person's neck when said body portion is disposed in an incision in said person's neck and projects into said person's trachea.

11. A tracheotomy tube as defined in claim 3, and in which a. said tubular body portion and said flange of said enlarged portion are composed of polyethylene,
b. said bushing is composed of aluminum, and
c. said inner cannula is
   (1) curved
   (2) substantially rigid, and
   (3) composed of acrylic resin.

12. A tracheotomy tube as defined in claim 1, and in which a. said collar includes a rear wall disposed in substantially parallel relation to said front wall,
b. said front and rear walls are disposed on respective opposite sides of a portion of said enlarged portion in position to hold said collar against axial displacement from said enlarged portion.

13. A tracheotomy tube as defined in claim 1, and in which a. said enlarged portion has an arcuate-shaped, radially outwardly facing annular recess extending between two abutment members defining the opposite extremities of said annular recess, and
b. said collar has an inner portion disposed in position to abuttingly engage respective ones of said abutment members when said collar is disposed in corresponding ones of said one and another positions, to thereby limit said rotation of said collar to rotation between said one and other positions.

* * * * *